(12) United States Patent
Pettitt et al.

(10) Patent No.: US 11,439,774 B2
(45) Date of Patent: Sep. 13, 2022

(54) VAPORIZER DEVICES AND CARTRIDGES WITH FOLDED MESH

(71) Applicant: JUUL Labs, Inc., San Francisco, CA (US)

(72) Inventors: Emily K. Pettitt, Cambridge (GB); Andrew J. Stratton, Royston (GB); James P. Westley, Cambridge (GB)

(73) Assignee: JUUL Labs, Inc., San Francisco, CA (US)

( * ) Notice: Subject to any disclaimer, the term of this patent is extended or adjusted under 35 U.S.C. 154(b) by 249 days.

(21) Appl. No.: 16/674,609

(22) Filed: Nov. 5, 2019

(65) Prior Publication Data
US 2020/0138115 A1 May 7, 2020

Related U.S. Application Data

(60) Provisional application No. 62/755,924, filed on Nov. 5, 2018.

(51) Int. Cl.
| | | |
|---|---|---|
| *A24F 13/00* | (2006.01) | |
| *A24F 17/00* | (2006.01) | |
| *A24F 25/00* | (2006.01) | |
| *A61M 11/04* | (2006.01) | |

(52) U.S. Cl.
CPC .................. *A61M 11/042* (2014.02)

(58) Field of Classification Search
CPC ..... A24F 40/46; A24F 40/485; A61M 11/042; A61M 15/006; A61M 16/209; A61M 2205/8206
See application file for complete search history.

(56) References Cited

U.S. PATENT DOCUMENTS

| | | |
|---|---|---|
| 4,947,874 A | 8/1990 | Brooks et al. |
| 4,947,875 A | 8/1990 | Brooks et al. |
| 5,060,671 A | 10/1991 | Counts et al. |
| | (Continued) | |

FOREIGN PATENT DOCUMENTS

| | | |
|---|---|---|
| CA | 2641869 A1 | 5/2010 |
| CA | 2935072 C | 5/2018 |
| | (Continued) | |

*Primary Examiner* — Abdullah A Riyami
*Assistant Examiner* — Thang H Nguyen
(74) *Attorney, Agent, or Firm* — Mintz Levin Cohn Ferris Glovsky and Popeo, P.C.

(57) ABSTRACT

Cartridges for vaporizer devices are provided. In one exemplary embodiment, the cartridge can include a reservoir housing, an airflow tube that extends through the reservoir housing, and a folded mesh that is disposed within the airflow tube and includes a plurality of folds. The airflow tube defines a passageway extending therethrough and at least a portion of the airflow tube is permeable to the vaporizable material, in which the permeable portion of the airflow tube is configured to draw vaporizable material from the reservoir housing into the airflow tube for vaporization. The folded mesh is configured to change from a deactivated state to an activated state in response to receiving an electric current, and when in the activated state, the folded mesh is configured to generate an amount of heat that is sufficient to vaporize at least a portion of the vaporizable material drawn from the reservoir housing. Vaporizer devices are also provided.

20 Claims, 3 Drawing Sheets

(56) References Cited

U.S. PATENT DOCUMENTS

| | | | |
|---|---|---|---|
| 5,505,214 A | 4/1996 | Collins et al. | |
| 5,666,978 A | 9/1997 | Counts et al. | |
| 6,026,820 A | 2/2000 | Baggett et al. | |
| 6,053,176 A | 4/2000 | Adams et al. | |
| 6,909,840 B2 | 6/2005 | Harwig et al. | |
| 7,726,320 B2 | 6/2010 | Robinson et al. | |
| 7,987,846 B2 | 8/2011 | Hale et al. | |
| 8,387,612 B2 | 3/2013 | Damani et al. | |
| 8,671,952 B2 | 3/2014 | Winterson et al. | |
| 8,851,068 B2 | 10/2014 | Cohen et al. | |
| 8,910,640 B2 | 12/2014 | Sears et al. | |
| 9,016,274 B1 | 4/2015 | White | |
| 9,226,525 B2 | 1/2016 | Liu | |
| 9,226,526 B2 | 1/2016 | Liu | |
| 9,289,014 B2 | 3/2016 | Tucker et al. | |
| 9,427,022 B2 | 8/2016 | Levin et al. | |
| 9,439,456 B2 | 9/2016 | Liu | |
| 9,497,997 B2 | 11/2016 | Wu | |
| 9,498,001 B2 | 11/2016 | Wu | |
| 9,510,623 B2 | 12/2016 | Tucker et al. | |
| 9,615,606 B2 | 4/2017 | Liu | |
| 9,648,908 B1 | 5/2017 | Rinehart et al. | |
| 9,681,688 B1 | 6/2017 | Rinehart et al. | |
| 9,687,025 B2 | 6/2017 | Cyphert et al. | |
| 9,687,028 B2 | 6/2017 | Park | |
| 9,723,874 B2 | 8/2017 | Liu | |
| 9,802,011 B2 | 10/2017 | Davidson et al. | |
| 9,814,262 B2 | 11/2017 | Peleg et al. | |
| 9,839,238 B2 | 12/2017 | Worm et al. | |
| 9,861,139 B2 | 1/2018 | Boldrini | |
| 9,956,357 B2 | 5/2018 | Chen | |
| 10,015,990 B2 | 7/2018 | Mironov | |
| 10,058,129 B2 | 8/2018 | Monsees et al. | |
| 10,076,137 B2 | 9/2018 | Krietzman | |
| 10,104,914 B2 | 10/2018 | Force | |
| 10,143,233 B2 | 12/2018 | Dubief et al. | |
| 10,143,234 B2 * | 12/2018 | Hon | H05B 3/22 |
| 10,299,514 B2 | 5/2019 | Bilat et al. | |
| 10,314,340 B2 | 6/2019 | Davis et al. | |
| 10,412,996 B2 | 9/2019 | Bright et al. | |
| 10,588,356 B2 | 3/2020 | Harrison et al. | |
| 11,083,229 B2 * | 8/2021 | Holtz | H05B 3/16 |
| 2003/0015045 A1 | 1/2003 | Yoshida et al. | |
| 2009/0192443 A1 | 7/2009 | Collins, Jr. | |
| 2009/0324206 A1 | 12/2009 | Young et al. | |
| 2011/0126831 A1 | 6/2011 | Fernandez Pernia | |
| 2012/0325227 A1 | 12/2012 | Robinson et al. | |
| 2013/0220315 A1 | 8/2013 | Conley et al. | |
| 2014/0174458 A1 | 6/2014 | Katz | |
| 2014/0190477 A1 | 7/2014 | Qiu | |
| 2014/0238423 A1 | 8/2014 | Tucker et al. | |
| 2014/0321837 A1 | 10/2014 | Flick | |
| 2014/0334804 A1 | 11/2014 | Choi | |
| 2015/0122278 A1 | 5/2015 | Hardgrove et al. | |
| 2015/0125136 A1 | 5/2015 | Sanchez | |
| 2015/0128967 A1 | 5/2015 | Robinson et al. | |
| 2015/0201674 A1 | 7/2015 | Dooly et al. | |
| 2015/0208731 A1 | 7/2015 | Malamud et al. | |
| 2015/0217068 A1 | 8/2015 | Wakalopulos | |
| 2015/0224268 A1 | 8/2015 | Henry et al. | |
| 2015/0237918 A1 | 8/2015 | Liu | |
| 2015/0245669 A1 | 9/2015 | Cadieux et al. | |
| 2015/0257445 A1 | 9/2015 | Henry et al. | |
| 2015/0258289 A1 | 9/2015 | Henry et al. | |
| 2015/0320116 A1 * | 11/2015 | Bleloch | A24F 40/465 219/628 |
| 2015/0335070 A1 | 11/2015 | Sears et al. | |
| 2015/0351456 A1 | 12/2015 | Johnson et al. | |
| 2016/0000149 A1 | 1/2016 | Scatterday | |
| 2016/0021934 A1 | 1/2016 | Cadieux et al. | |
| 2016/0044962 A1 | 2/2016 | Thorens et al. | |
| 2016/0128390 A1 | 5/2016 | Liu | |
| 2016/0143362 A1 | 5/2016 | Boldrini | |
| 2016/0144458 A1 | 5/2016 | Boldrini | |
| 2016/0157523 A1 | 6/2016 | Liu | |
| 2016/0183595 A1 | 6/2016 | Grimandi et al. | |
| 2016/0271347 A1 | 9/2016 | Raichman | |
| 2016/0295922 A1 | 10/2016 | John et al. | |
| 2016/0309785 A1 | 10/2016 | Holtz | |
| 2016/0309786 A1 | 10/2016 | Holtz et al. | |
| 2016/0338407 A1 | 11/2016 | Kerdemelidis | |
| 2016/0338410 A1 | 11/2016 | Batista et al. | |
| 2016/0345630 A1 | 12/2016 | Mironov et al. | |
| 2016/0345632 A1 | 12/2016 | Lipowicz et al. | |
| 2017/0006921 A1 | 1/2017 | Lemay et al. | |
| 2017/0027226 A1 | 2/2017 | Mironov et al. | |
| 2017/0027227 A1 | 2/2017 | Lipowicz | |
| 2017/0035109 A1 * | 2/2017 | Liu | A24F 40/42 |
| 2017/0035112 A1 | 2/2017 | Thorens | |
| 2017/0035113 A1 | 2/2017 | Thorens | |
| 2017/0108840 A1 | 4/2017 | Hawes et al. | |
| 2017/0127727 A1 | 5/2017 | Davidson et al. | |
| 2017/0136196 A1 | 5/2017 | Davidson et al. | |
| 2017/0143041 A1 | 5/2017 | Batista et al. | |
| 2017/0150755 A1 | 6/2017 | Batista | |
| 2017/0164657 A1 | 6/2017 | Batista | |
| 2017/0188635 A1 | 7/2017 | Force et al. | |
| 2017/0208858 A1 | 7/2017 | Li | |
| 2017/0231283 A1 | 8/2017 | Gadas | |
| 2017/0245551 A1 | 8/2017 | Reevell | |
| 2017/0258143 A1 | 9/2017 | Lederer | |
| 2017/0273358 A1 | 9/2017 | Batista et al. | |
| 2017/0280775 A1 | 10/2017 | Manca et al. | |
| 2017/0280776 A1 | 10/2017 | Manca et al. | |
| 2017/0280778 A1 | 10/2017 | Force | |
| 2017/0354184 A1 | 12/2017 | Mironov et al. | |
| 2017/0360093 A1 | 12/2017 | Fernando | |
| 2018/0116284 A1 | 5/2018 | Biel et al. | |
| 2018/0116285 A1 | 5/2018 | Polloni et al. | |
| 2018/0116286 A1 | 5/2018 | Polloni et al. | |
| 2018/0117268 A1 | 5/2018 | Selby et al. | |
| 2018/0125120 A1 * | 5/2018 | Gavrielov | H05B 3/44 |
| 2018/0132532 A1 | 5/2018 | Batista | |
| 2018/0177240 A1 | 6/2018 | Duque et al. | |
| 2018/0184712 A1 | 7/2018 | Fraser et al. | |
| 2018/0192700 A1 | 7/2018 | Fraser et al. | |
| 2018/0242642 A1 * | 8/2018 | Silvesstrini | H05B 3/03 |
| 2018/0360116 A1 * | 12/2018 | Schmidt | H05B 3/34 |
| 2019/0001077 A1 * | 1/2019 | Xu | A24F 40/44 |
| 2019/0053535 A1 * | 2/2019 | Apetrei Birza | A24B 15/167 |
| 2019/0069598 A1 | 3/2019 | Liu | |
| 2019/0166908 A1 | 6/2019 | Liu | |
| 2020/0281264 A1 * | 9/2020 | Wright | A24F 40/40 |
| 2021/0015148 A1 * | 1/2021 | Shenton | A24F 40/20 |
| 2021/0321663 A1 * | 10/2021 | Hagen | B65D 25/108 |

FOREIGN PATENT DOCUMENTS

| | | |
|---|---|---|
| CA | 2949516 C | 6/2019 |
| CN | 104116138 A | 10/2014 |
| CN | 104968225 A | 10/2015 |
| CN | 206462409 U | 9/2017 |
| CN | 104055223 B | 10/2017 |
| CN | 206650418 U | 11/2017 |
| CN | 107411172 A | 12/2017 |
| CN | 206821974 U | 1/2018 |
| CN | 207285198 U | 5/2018 |
| CN | 207476951 U | 6/2018 |
| CN | 208030261 U | 11/2018 |
| CN | 208113970 U | 11/2018 |
| CN | 109588779 A | 4/2019 |
| CN | 105899094 B | 5/2019 |
| CN | 106028857 B | 5/2019 |
| CN | 107889450 B | 8/2020 |
| DE | 102006004484 A1 | 8/2007 |
| EP | 3216359 A1 | 9/2017 |
| EP | 2789250 B1 | 12/2018 |
| EP | 3155908 B1 | 12/2018 |
| EP | 3117860 B1 | 1/2019 |
| EP | 3232834 B1 | 4/2019 |
| EP | 2850956 B1 | 6/2019 |
| KR | 200461404 Y1 | 7/2012 |
| KR | 20180083424 A | 7/2018 |
| TW | 201436722 A | 10/2014 |

(56) References Cited

FOREIGN PATENT DOCUMENTS

| | | |
|---|---|---|
| UA | 88052 C2 | 9/2009 |
| WO | WO 03034847 A1 | 5/2003 |
| WO | WO 2013040193 A2 | 3/2013 |
| WO | WO 2013044537 A1 | 4/2013 |
| WO | WO-2013083634 A1 | 6/2013 |
| WO | WO-2013083638 A1 | 6/2013 |
| WO | WO 2013174001 A1 | 11/2013 |
| WO | WO 2014144678 A2 | 9/2014 |
| WO | WO 2015026081 A1 | 2/2015 |
| WO | WO 2015037925 A1 | 3/2015 |
| WO | WO 2015109476 A1 | 7/2015 |
| WO | WO 2016009202 A1 | 1/2016 |
| WO | WO 2016019573 A1 | 2/2016 |
| WO | WO 2016023173 A1 | 2/2016 |
| WO | WO 2016099276 A1 | 6/2016 |
| WO | WO 2016110522 A1 | 7/2016 |
| WO | WO 2016119496 A1 | 8/2016 |
| WO | WO 2016131755 A1 | 8/2016 |
| WO | WO 2016138689 A1 | 9/2016 |
| WO | WO-2016172441 A1 | 10/2016 |
| WO | WO 2016174179 A1 | 11/2016 |
| WO | WO 2016179376 A1 | 11/2016 |
| WO | WO 2017024478 A1 | 2/2017 |
| WO | WO 2017085240 A1 | 5/2017 |
| WO | WO 2017097821 A1 | 6/2017 |
| WO | WO 2017108268 A1 | 6/2017 |
| WO | WO 2017122196 A1 | 7/2017 |
| WO | WO 2017156743 A1 | 9/2017 |
| WO | WO 2017167513 A1 | 10/2017 |
| WO | WO 2018122978 A1 | 7/2018 |
| WO | WO-2020000869 A1 | 1/2020 |
| WO | WO 2020023547 A1 | 1/2020 |
| WO | WO-2020025654 A1 | 2/2020 |

\* cited by examiner

VAPORIZER DEVICES AND CARTRIDGES WITH FOLDED MESH

CROSS-REFERENCE TO RELATED APPLICATIONS

This application claims priority to U.S. Provisional Patent Application No. 62/755,924 filed on Nov. 5, 2018, and entitled "Cartridges For Vaporizer Devices," the disclosure of which is incorporated herein by reference in its entirety.

TECHNICAL FIELD

The subject matter described herein relates to vaporizer devices, including vaporizer cartridges.

BACKGROUND

Vaporizer devices, which can also be referred to as vaporizers, electronic vaporizer devices, or e-vaporizer devices, can be used for delivery of an aerosol (for example, a vapor-phase and/or condensed-phase material suspended in a stationary or moving mass of air or some other gas carrier) containing one or more active ingredients by inhalation of the aerosol by a user of the vaporizing device. For example, electronic nicotine delivery systems (ENDS) include a class of vaporizer devices that are battery powered and that can be used to simulate the experience of smoking, but without burning of tobacco or other substances. Vaporizer devices are gaining increasing popularity both for prescriptive medical use, in delivering medicaments, and for consumption of tobacco, nicotine, and other plant-based materials. Vaporizer devices can be portable, self-contained, and/or convenient for use.

In use of a vaporizer device, the user inhales an aerosol, colloquially referred to as "vapor," which can be generated by a heating element that vaporizes (e.g., causes a liquid or solid to at least partially transition to the gas phase) a vaporizable material, which can be liquid, a solution, a solid, a paste, a wax, and/or any other form compatible for use with a specific vaporizer device. The vaporizable material used with a vaporizer device can be provided within a cartridge for example, a separable part of the vaporizer device that contains vaporizable material) that includes an outlet (for example, a mouthpiece) for inhalation of the aerosol by a user.

To receive the inhalable aerosol generated by a vaporizer device, a user may, in certain examples, activate the vaporizer device by taking a puff, by pressing a button, and/or by some other approach. A puff as used herein can refer to inhalation by the user in a manner that causes a volume of air to be drawn into the vaporizer device such that the inhalable aerosol is generated by a combination of the vaporized vaporizable material with the volume of air.

Vaporizer devices can be controlled by one or more controllers, electronic circuits (for example, sensors, heating elements), and/or the like on the vaporizer device. Vaporizer devices can also wirelessly communicate with an external controller for example, a computing device such as a smartphone).

A vaporize device typically uses an atomizer that heats the vaporizable material and delivers an inhalable aerosol instead of smoke. The atomizer can include a wicking element that conveys an amount of a vaporizable material (along its length) to a part of the atomizer that includes a heating element. In some embodiments, the atomizer includes a mesh that can be used as a wicking element, which draws the vaporizable material into the atomizer, or can be used as a heating element, which vaporizes the vaporizable material. As such, the use of a mesh therefore requires the atomizer to include an additional element to either draw the vaporizable material into the atomizer or heat the vaporizable material depending on how the mesh is being used. For example, in instances where the meshes are used as the wicking element, an additional heater is required used because the electrical resistance of the mesh is generally low. In other instances where the mesh is used as the heating element, an additional wicking element is needed, such as cotton. As such, improved vaporizer devices and/or vaporizer cartridges that improve upon or overcome these issues is desired.

SUMMARY

Aspects of the current subject matter relate to vaporizer devices and to cartridges for use in a vaporizer device.

In some variations, one or more of the following features may optionally be included in any feasible combination.

In one exemplary embodiment, a cartridge is provided and includes a reservoir housing that is configured to hold a vaporizable material, an airflow tube that extends through the reservoir housing, and a folded mesh that is disposed within the airflow tube and includes a plurality of folds. The airflow tube defines a passageway extending therethrough and at least a portion of the airflow tube being permeable to the vaporizable material, in which the permeable portion of the airflow tube is configured to draw the vaporizable material from the reservoir housing into the airflow tube for vaporization. The folded mesh is configured to change from a deactivated state to an activated state in response to receiving an electric current, and when in the activated state, the folded mesh is configured to generate an amount of heat that is sufficient to vaporize at least a portion of the vaporizable material drawn from the reservoir housing.

In some embodiments, the permeable portion of the airflow tube can include a plurality of holes.

The folded mesh can have a variety of configurations. For example, in some embodiments, the folded mesh can extend a mesh length from a first end to a second end, in which the mesh length of the folded mesh can be less than a predetermined length of the folded mesh in an unfolded state. The folded mesh can have a width that can be greater than a radius of the airflow tube.

The airflow tube can have a variety of configurations. For example, in some embodiments, the airflow tube can have a tube length that extends from a first end to a second end. The tube length can be greater than the mesh length.

In some embodiments, a pressure equilibrium can be created across the permeable portion of the airflow tube between the reservoir housing and the passageway when the folded mesh is in the deactivated state.

In some embodiments, a pressure differential can be created across the permeable portion of the airflow tube between the reservoir housing and the passageway when the folded mesh is in the activated state. The pressure differential can be created in response to the vaporization of at least a portion of the vaporizable material when the folded mesh is in the activated state. In certain embodiments, the vaporizable material can flow from the reservoir housing into the airflow tube through the permeable portion of the airflow tube when the pressure differential is created.

In some embodiments, a portion of the vaporizable material can be within the airflow tube when the folded mesh is in the deactivated state.

In another exemplary embodiment, a vaporizer device is provided and includes a vaporizer body and a cartridge that is selectively coupled to and removable from the vaporizer body. The cartridge includes a reservoir housing that is configured to hold a vaporizable material, an airflow tube that extends through the reservoir housing, and a folded mesh that is disposed within the airflow tube and includes a plurality of folds. The airflow tube defines a passageway extending therethrough and at least a portion of the airflow tube being permeable to the vaporizable material, in which the permeable portion of the airflow tube is configured to draw the vaporizable material from the reservoir housing into the airflow tube for vaporization. The folded mesh is configured to change from a deactivated state to an activated state in response to receiving an electric current, and when in the activated state, the folded mesh is configured to generate an amount of heat that is sufficient to vaporize at least a portion of the vaporizable material drawn from the reservoir housing.

The vaporizer body can have a variety of configurations. In some embodiments, the vaporizer body can include a power source.

In some embodiments, the permeable portion of the airflow tube can include a plurality of holes.

The folded mesh can have a variety of configurations. For example, in some embodiments, the folded mesh can extend a mesh length from a first end to a second end, in which the mesh length of the folded mesh can be less than a predetermined length of the folded mesh in an unfolded state. The folded mesh can have a width that can be greater than a radius of the airflow tube.

In some embodiments, a pressure equilibrium can be created across the permeable portion of the airflow tube between the reservoir housing and the passageway when the folded mesh is in the deactivated state.

In some embodiments, a pressure differential can be created across the permeable portion of the airflow tube between the reservoir housing and the passageway when the folded mesh is in the activated state. The pressure differential can be created in response to the vaporization of at least a portion of the vaporizable material when the folded mesh is in the activated state. In certain embodiments, the vaporizable material can flow from the reservoir housing into the airflow tube through the permeable portion of the airflow tube when the pressure differential is created.

In some embodiments, a portion of the vaporizable material can be within the airflow tube when the folded mesh is in the deactivated state.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter.

BRIEF DESCRIPTION OF THE DRAWINGS

The accompanying drawings, which are incorporated into and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Implementations of the current subject matter include methods, apparatuses, articles of manufacture, and systems relating to vaporization of one or more materials for inhalation by a user. Example implementations include vaporizer devices and systems including vaporizer devices. The term "vaporizer device" as used in the following description and claims refers to any of a self-contained apparatus, an apparatus that includes two or more separable parts (for example, a vaporizer body that includes a battery and other hardware, and a cartridge that includes a vaporizable material), and/or the like. A "vaporizer system," as used herein, can include one or more components, such as a vaporizer device. Examples of vaporizer devices consistent with implementations of the current subject matter include electronic vaporizers, electronic nicotine delivery systems (ENDS), and/or the like. In general, such vaporizer devices are hand-held devices that heat (such as by convection, conduction, radiation, and/or some combination thereof) a vaporizable material to provide an inhalable dose of the material.

The vaporizable material used with a vaporizer device can be provided within a cartridge (for example, a part of the vaporizer device that contains the vaporizable material in a reservoir or other container) which can be refillable when empty, or disposable such that a new cartridge containing additional vaporizable material of a same or different type can be used). A vaporizer device can be a cartridge-using vaporizer device, a cartridge-less vaporizer device, or a multi-use vaporizer device capable of use with or without a cartridge. For example, a vaporizer device can include a heating chamber (for example, an oven or other region in which material is heated by a heating element) configured to receive a vaporizable material directly into the heating chamber, and/or a reservoir or the like for containing the vaporizable material.

In some implementations, a vaporizer device can be configured for use with a liquid vaporizable material (for example, a carrier solution in which an active and/or inactive ingredient(s) are suspended or held in solution, or a liquid form of the vaporizable material itself). The liquid vaporizable material can be capable of being completely vaporized. Alternatively, at least a portion of the liquid vaporizable material can remain after all of the material suitable for inhalation has been vaporized.

Figure 1A:
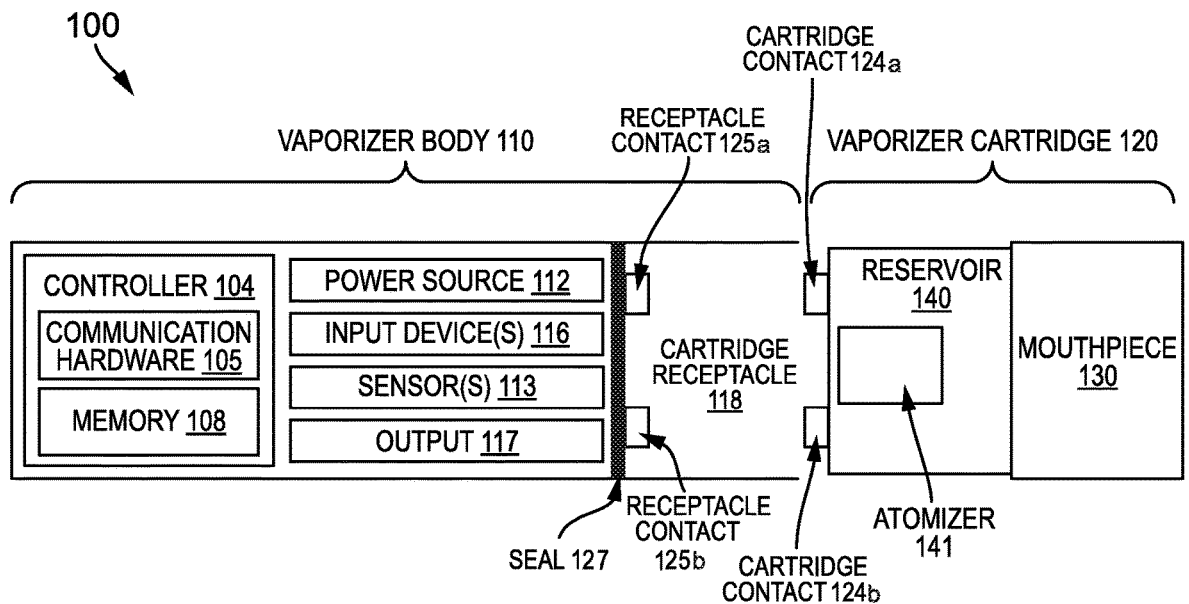
FIG. 1A is a block diagram of a vaporizer device.

Referring to the block diagram of FIG. 1A, a vaporizer device 100 can include a power source 112 (for example, a battery, which can be a rechargeable battery), and a controller 104 (for example, a processor, circuitry, etc. capable of executing logic) for controlling delivery of heat to an atomizer 141 to cause a vaporizable material 102 to be converted from a condensed form (such as a liquid, a solution, a suspension, a part of an at least partially unprocessed plant material, etc.) to the gas phase. The controller 104 can be part of one or more printed circuit boards (PCBs) consistent with certain implementations of the current subject matter.

After conversion of the vaporizable material 102 to the gas phase, at least some of the vaporizable material 102 in the gas phase can condense to form particulate matter in at least a partial local equilibrium with the gas phase as part of an aerosol, which can form some or all of an inhalable dose provided by the vaporizer device 100 during a user's puff or draw on the vaporizer device 100. It should be appreciated that the interplay between gas and condensed phases in an aerosol generated by a vaporizer device 100 can be complex and dynamic, due to factors such as ambient temperature, relative humidity, chemistry, flow conditions in airflow paths (both inside the vaporizer device and in the airways of a human or other animal), and/or mixing of the vaporizable material 102 in the gas phase or in the aerosol phase with other air streams, which can affect one or more physical parameters of an aerosol. In some vaporizer devices, and particularly for vaporizer devices configured for delivery of volatile vaporizable materials, the inhalable dose can exist predominantly in the gas phase (for example, formation of condensed phase particles can be very limited).

The atomizer 141 in the vaporizer device 100 can be configured to vaporize a vaporizable material 102. The vaporizable material 102 can be a liquid. Examples of the vaporizable material 102 include neat liquids, suspensions, solutions, mixtures, and/or the like. The atomizer 141 can include a wicking element (i.e., a wick) configured to convey an amount of the vaporizable material 102 to a part of the atomizer 141 that includes a heating element (not shown in FIG. 1A).

For example, the wicking element can be configured to draw the vaporizable material 102 from a reservoir 140 configured to contain the vaporizable material 102, such that the vaporizable material 102 can be vaporized by heat delivered from a heating element. The wicking element can also optionally allow air to enter the reservoir 140 and replace the volume of vaporizable material 102 removed. In some implementations of the current subject matter, capillary action can pull vaporizable material 102 into the wick for vaporization by the heating element, and air can return to the reservoir 140 through the wick to at least partially equalize pressure in the reservoir 140. Other methods of allowing air back into the reservoir 140 to equalize pressure are also within the scope of the current subject matter.

As used herein, the terms "wick" or "wicking element" include any material capable of causing fluid motion via capillary pressure.

The heating element can include one or more of a conductive heater, a radiative heater, and/or a convective heater. One type of heating element is a resistive heating element, which can include a material (such as a metal or alloy, for example a nickel-chromium alloy, or a non-metallic resistor) configured to dissipate electrical power in the form of heat when electrical current is passed through one or more resistive segments of the heating element. In some implementations of the current subject matter, the atomizer 141 can include a heating element which includes a resistive coil or other heating element wrapped around, positioned within, integrated into a bulk shape of, pressed into thermal contact with, or otherwise arranged to deliver heat to a wicking element, to cause the vaporizable material 102 drawn from the reservoir 140 by the wicking element to be vaporized for subsequent inhalation by a user in a gas and/or a condensed (for example, aerosol particles or droplets) phase. Other wicking elements, heating elements, and/or atomizer assembly configurations are also possible.

The heating element can be activated in association with a user puffing (i.e., drawing, inhaling, etc.) on a mouthpiece 130 of the vaporizer device 100 to cause air to flow from an air inlet, along an airflow path that passes the atomizer 141 (i.e., wicking element and heating element). Optionally, air can flow from an air inlet through one or more condensation areas or chambers, to an air outlet in the mouthpiece 130. Incoming air moving along the airflow path moves over or through the atomizer 141, where vaporizable material 102 in the gas phase is entrained into the air. The heating element can be activated via the controller 104, which can optionally be a part of a vaporizer body 110 as discussed herein, causing current to pass from the power source 112 through a circuit including the resistive heating element, which is optionally part of a vaporizer cartridge 120 as discussed herein. As noted herein, the entrained vaporizable material 102 in the gas phase can condense as it passes through the remainder of the airflow path such that an inhalable dose of the vaporizable material 102 in an aerosol form can be delivered from the air outlet (for example, the mouthpiece 130) for inhalation by a user.

Activation of the heating element can be caused by automatic detection of a puff based on one or more signals generated by one or more of a sensor 113. The sensor 113 and the signals generated by the sensor 113 can include one or more of: a pressure sensor or sensors disposed to detect pressure along the airflow path relative to ambient pressure (or optionally to measure changes in absolute pressure), a motion sensor or sensors (for example, an accelerometer) of the vaporizer device 100, a flow sensor or sensors of the vaporizer device 100, a capacitive lip sensor of the vaporizer device 100, detection of interaction of a user with the vaporizer device 100 via one or more input devices 116 (for example, buttons or other tactile control devices of the vaporizer device 100), receipt of signals from a computing device in communication with the vaporizer device 100, and/or via other approaches for determining that a puff is occurring or imminent.

As discussed herein, the vaporizer device 100 consistent with implementations of the current subject matter can be configured to connect (such as, for example, wirelessly or via a wired connection) to a computing device (or optionally two or more devices) in communication with the vaporizer device 100. To this end, the controller 104 can include communication hardware 105. The controller 104 can also include a memory 108. The communication hardware 105 can include firmware and/or can be controlled by software for executing one or more cryptographic protocols for the communication.

A computing device can be a component of a vaporizer system that also includes the vaporizer device 100, and can include its own hardware for communication, which can establish a wireless communication channel with the communication hardware 105 of the vaporizer device 100. For example, a computing device used as part of a vaporizer system can include a general-purpose computing device (such as a smartphone, a tablet, a personal computer, some other portable device such as a smartwatch, or the like) that executes software to produce a user interface for enabling a user to interact with the vaporizer device 100. In other implementations of the current subject matter, such a device used as part of a vaporizer system can be a dedicated piece of hardware such as a remote control or other wireless or wired device having one or more physical or soft (i.e., configurable on a screen or other display device and selectable via a user interaction with a touch-sensitive screen or some other input device like a mouse, pointer, trackball, cursor buttons, or the like) interface controls. The vaporizer device 100 can also include one or more outputs 117 or devices for providing information to the user. For example, the outputs 117 can include one or more light emitting diodes (LEDs) configured to provide feedback to a user based on a status and/or mode of operation of the vaporizer device 100.

In the example in which a computing device provides signals related to activation of the resistive heating element, or in other examples of coupling of a computing device with the vaporizer device 100 for implementation of various control or other functions, the computing device executes one or more computer instruction sets to provide a user interface and underlying data handling. In one example, detection by the computing device of user interaction with one or more user interface elements can cause the computing device to signal the vaporizer device 100 to activate the heating element to reach an operating temperature for creation of an inhalable dose of vapor/aerosol. Other functions of the vaporizer device 100 can be controlled by interaction of a user with a user interface on a computing device in communication with the vaporizer device 100.

The temperature of a resistive heating element of the vaporizer device 100 can depend on a number of factors, including an amount of electrical power delivered to the resistive heating element and/or a duty cycle at which the electrical power is delivered, conductive heat transfer to other parts of the electronic vaporizer device 100 and/or to the environment, latent heat losses due to vaporization of the vaporizable material 102 from the wicking element and/or the atomizer 141 as a whole, and convective heat losses due to airflow (i.e., air moving across the heating element or the atomizer 141 as a whole when a user inhales on the vaporizer device 100). As noted herein, to reliably activate the heating element or heat the heating element to a desired temperature, the vaporizer device 100 may, in some implementations of the current subject matter, make use of signals from the sensor 113 (for example, a pressure sensor) to determine when a user is inhaling. The sensor 113 can be positioned in the airflow path and/or can be connected (for example, by a passageway or other path) to an airflow path containing an inlet for air to enter the vaporizer device 100 and an outlet via which the user inhales the resulting vapor and/or aerosol such that the sensor 113 experiences changes (for example, pressure changes) concurrently with air passing through the vaporizer device 100 from the air inlet to the air outlet. In some implementations of the current subject matter, the heating element can be activated in association with a user's puff, for example by automatic detection of the puff, or by the sensor 113 detecting a change (such as a pressure change) in the airflow path.

The sensor 113 can be positioned on or coupled to (i.e., electrically or electronically connected, either physically or via a wireless connection) the controller 104 (for example, a printed circuit board assembly or other type of circuit board). To take measurements accurately and maintain durability of the vaporizer device 100, it can be beneficial to provide a seal 127 resilient enough to separate an airflow path from other parts of the vaporizer device 100. The seal 127, which can be a gasket, can be configured to at least partially surround the sensor 113 such that connections of the sensor 113 to the internal circuitry of the vaporizer device 100 are separated from a part of the sensor 113 exposed to the airflow path. In an example of a cartridge-based vaporizer device, the seal 127 can also separate parts of one or more electrical connections between the vaporizer body 110 and the vaporizer cartridge 120. Such arrangements of the seal 127 in the vaporizer device 100 can be helpful in mitigating against potentially disruptive impacts on vaporizer components resulting from interactions with environmental factors such as water in the vapor or liquid phases, other fluids such as the vaporizable material 102, etc., and/or to reduce the escape of air from the designated airflow path in the vaporizer device 100. Unwanted air, liquid or other fluid passing and/or contacting circuitry of the vaporizer device 100 can cause various unwanted effects, such as altered pressure readings, and/or can result in the buildup of unwanted material, such as moisture, excess vaporizable material 102, etc., in parts of the vaporizer device 100 where they can result in poor pressure signal, degradation of the sensor 113 or other components, and/or a shorter life of the vaporizer device 100. Leaks in the seal 127 can also result in a user inhaling air that has passed over parts of the vaporizer device 100 containing, or constructed of, materials that may not be desirable to be inhaled.

In some implementations, the vaporizer body 110 includes the controller 104, the power source 112 (for example, a battery), one more of the sensor 113, charging contacts (such as those for charging the power source 112), the seal 127, and a cartridge receptacle 118 configured to receive the vaporizer cartridge 120 for coupling with the vaporizer body 110 through one or more of a variety of attachment structures. In some examples, the vaporizer cartridge 120 includes the reservoir 140 for containing the vaporizable material 102, and the mouthpiece 130 has an aerosol outlet for delivering an inhalable dose to a user. The vaporizer cartridge 120 can include the atomizer 141 having a wicking element and a heating element. Alternatively, one or both of the wicking element and the heating element can be part of the vaporizer body 110. In implementations in which any part of the atomizer 141 (i.e., heating element and/or wicking element) is part of the vaporizer body 110, the vaporizer device 100 can be configured to supply vaporizable material 102 from the reservoir 140 in the vaporizer cartridge 120 to the part(s) of the atomizer 141 included in the vaporizer body 110.

In an embodiment of the vaporizer device 100 in which the power source 112 is part of the vaporizer body 110, and a heating element is disposed in the vaporizer cartridge 120 and configured to couple with the vaporizer body 110, the vaporizer device 100 can include electrical connection features (for example, means for completing a circuit) for completing a circuit that includes the controller 104 (for example, a printed circuit board, a microcontroller, or the like), the power source 112, and the heating element (for example, a heating element within the atomizer 141). These features can include one or more contacts (referred to herein as cartridge contacts 124a and 124b) on a bottom surface of the vaporizer cartridge 120 and at least two contacts (referred to herein as receptacle contacts 125a and 125b) disposed near a base of the cartridge receptacle 118 of the vaporizer device 100 such that the cartridge contacts 124a and 124b and the receptacle contacts 125a and 125b make electrical connections when the vaporizer cartridge 120 is inserted into and coupled with the cartridge receptacle 118. The circuit completed by these electrical connections can allow delivery of electrical current to a heating element and can further be used for additional functions, such as measuring a resistance of the heating element for use in determining and/or controlling a temperature of the heating element based on a thermal coefficient of resistivity of the heating element.

In some implementations of the current subject matter, the cartridge contacts 124*a* and 124*b* and the receptacle contacts 125*a* and 125*b* can be configured to electrically connect in either of at least two orientations. In other words, one or more circuits necessary for operation of the vaporizer device 100 can be completed by insertion of the vaporizer cartridge 120 into the cartridge receptacle 118 in a first rotational orientation (around an axis along which the vaporizer cartridge 120 is inserted into the cartridge receptacle 118 of the vaporizer body 110) such that the cartridge contact 124*a* is electrically connected to the receptacle contact 125*a* and the cartridge contact 124*b* is electrically connected to the receptacle contact 125*b*. Furthermore, the one or more circuits necessary for operation of the vaporizer device 100 can be completed by insertion of the vaporizer cartridge 120 in the cartridge receptacle 118 in a second rotational orientation such cartridge contact 124*a* is electrically connected to the receptacle contact 125*b* and cartridge contact 124*b* is electrically connected to the receptacle contact 125*a*.

For example, the vaporizer cartridge 120 or at least the insertable end 122 of the vaporizer cartridge 120 can be symmetrical upon a rotation of 180° around an axis along which the vaporizer cartridge 120 is inserted into the cartridge receptacle 118. In such a configuration, the circuitry of the vaporizer device 100 can support identical operation regardless of which symmetrical orientation of the vaporizer cartridge 120 occurs.

In one example of an attachment structure for coupling the vaporizer cartridge 120 to the vaporizer body 110, the vaporizer body 110 includes one or more detents (for example, dimples, protrusions, etc.) protruding inwardly from an inner surface of the cartridge receptacle 118, additional material (such as metal, plastic, etc.) formed to include a portion protruding into the cartridge receptacle 118, and/or the like. One or more exterior surfaces of the vaporizer cartridge 120 can include corresponding recesses (not shown in FIG. 1A) that can fit and/or otherwise snap over such detents or protruding portions when the vaporizer cartridge 120 is inserted into the cartridge receptacle 118 on the vaporizer body 110. When the vaporizer cartridge 120 and the vaporizer body 110 are coupled (e.g., by insertion of the vaporizer cartridge 120 into the cartridge receptacle 118 of the vaporizer body 110), the detents or protrusions of the vaporizer body 110 can fit within and/or otherwise be held within the recesses of the vaporizer cartridge 120, to hold the vaporizer cartridge 120 in place when assembled. Such an assembly can provide enough support to hold the vaporizer cartridge 120 in place to ensure good contact between the cartridge contacts 124*a* and 124*b* and the receptacle contacts 125*a* and 125*b*, while allowing release of the vaporizer cartridge 120 from the vaporizer body 110 when a user pulls with reasonable force on the vaporizer cartridge 120 to disengage the vaporizer cartridge 120 from the cartridge receptacle 118.

In some implementations, the vaporizer cartridge 120, or at least an insertable end 122 of the vaporizer cartridge 120 configured for insertion in the cartridge receptacle 118, can have a non-circular cross section transverse to the axis along which the vaporizer cartridge 120 is inserted into the cartridge receptacle 118. For example, the non-circular cross section can be approximately rectangular, approximately elliptical (i.e., have an approximately oval shape), non-rectangular but with two sets of parallel or approximately parallel opposing sides (i.e., having a parallelogram-like shape), or other shapes having rotational symmetry of at least order two. In this context, approximate shape indicates that a basic likeness to the described shape is apparent, but that sides of the shape in question need not be completely linear and vertices need not be completely sharp. Rounding of both or either of the edges or the vertices of the cross-sectional shape is contemplated in the description of any non-circular cross section referred to herein.

The cartridge contacts 124*a* and 124*b* and the receptacle contacts 125*a* and 125*b* can take various forms. For example, one or both sets of contacts can include conductive pins, tabs, posts, receiving holes for pins or posts, or the like. Some types of contacts can include springs or other features to facilitate better physical and electrical contact between the contacts on the vaporizer cartridge 120 and the vaporizer body 110. The electrical contacts can optionally be gold-plated, and/or include other materials.

Figure 1B:
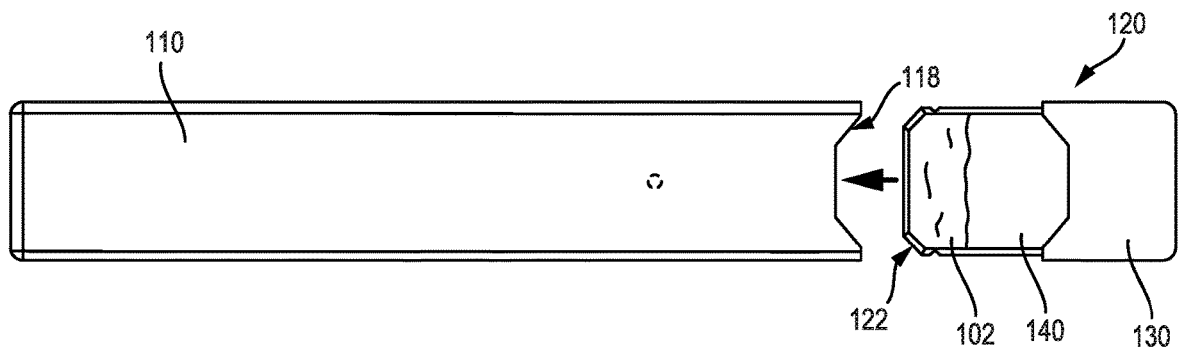
FIG. 1B is a top view of an embodiment of a vaporizer device, showing a vaporizer cartridge separated from a vaporizer device body.
Figure 1C:
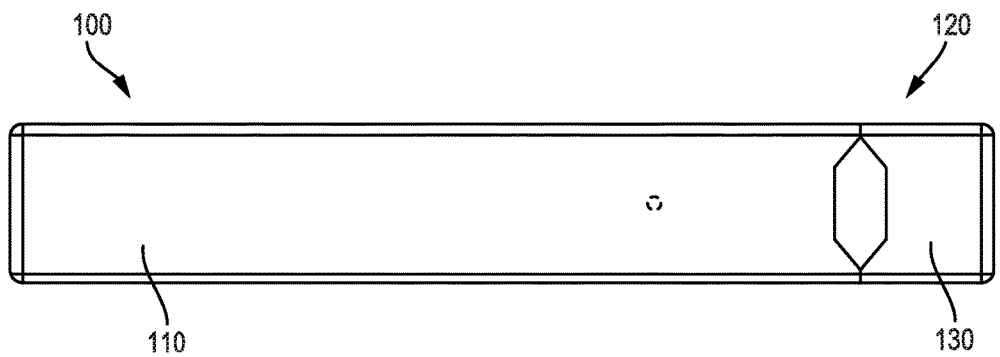
FIG. 1C is a top view of the vaporizer device of FIG. 1B, showing the vaporizer cartridge coupled to the vaporizer device body.
Figure 1D:
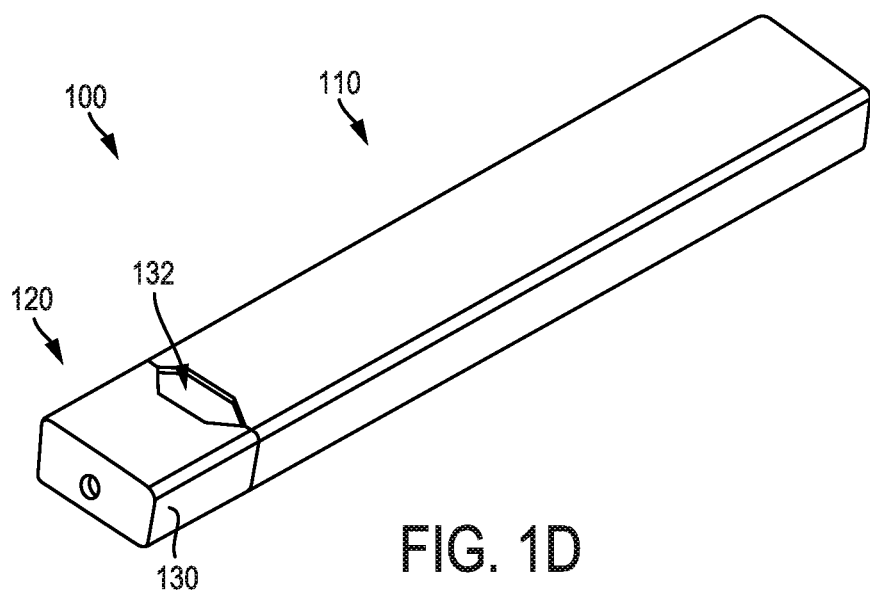
FIG. 1D is a perspective view of the vaporizer device of FIG. 1C.

FIGS. 1B-1D illustrate an embodiment of the vaporizer body 110 having a cartridge receptacle 118 into which the vaporizer cartridge 120 can be releasably inserted. FIGS. 1B and 1C show top views of the vaporizer device 100 illustrating the vaporizer cartridge 120 being positioned for insertion and inserted, respectively, into the vaporizer body 110. FIG. 1D illustrates the reservoir 140 of the vaporizer cartridge 120 being formed in whole or in part from translucent material such that a level of the vaporizable material 102 is visible from a window 132 (e.g., translucent material) along the vaporizer cartridge 120. The vaporizer cartridge 120 can be configured such that the window 132 remains visible when insertably received by the vaporizer cartridge receptacle 118 of the vaporizer body 110. For example, in one exemplary configuration, the window 132 can be disposed between a bottom edge of the mouthpiece 130 and a top edge of the vaporizer body 110 when the vaporizer cartridge 120 is coupled with the cartridge receptacle 118.

Figure 1E:
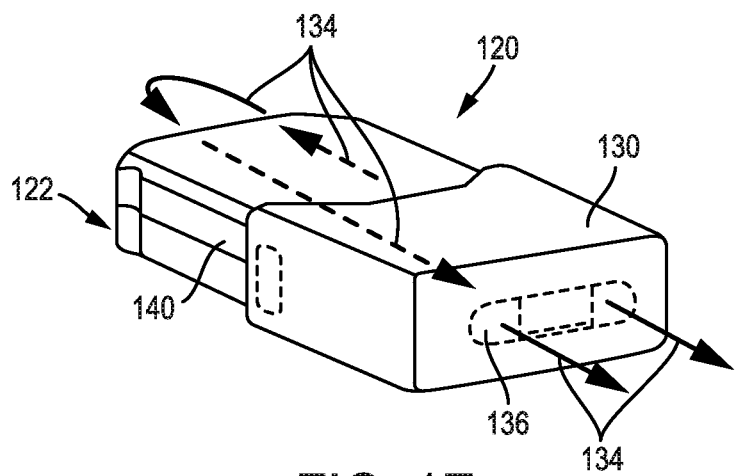
FIG. 1E is a perspective view of the vaporizer cartridge of FIG. 1B.

FIG. 1E illustrates an example airflow path 134 created during a puff by a user on the vaporizer device 100. The airflow path 134 can direct air to a vaporization chamber 150 (see FIG. 1F) contained in a wick housing where the air is combined with inhalable aerosol for delivery to a user via a mouthpiece 130, which can also be part of the vaporizer cartridge 120. For example, when a user puffs on the vaporizer device 100 device 100, air can pass between an outer surface of the vaporizer cartridge 120 (for example, window 132 shown in FIG. 1D) and an inner surface of the cartridge receptacle 118 on the vaporizer body 110. Air can then be drawn into the insertable end 122 of the vaporizer cartridge 120, through the vaporization chamber 150 that includes or contains the heating element and wick, and out through an outlet 136 of the mouthpiece 130 for delivery of the inhalable aerosol to a user.

As shown in FIG. 1E, this configuration causes air to flow down around the insertable end 122 of the vaporizer cartridge 120 into the cartridge receptacle 118 and then flow back in the opposite direction after passing around the insertable end 122 (e.g., an end opposite of the end including the mouthpiece 130) of the vaporizer cartridge 120 as it enters into the cartridge body toward the vaporization chamber 150. The airflow path 134 then travels through the interior of the vaporizer cartridge 120, for example via one or more tubes or internal channels (such as cannula 128 shown in FIG. 1F) and through one or more outlets (such as outlet 136) formed in the mouthpiece 130. The mouthpiece 130 can be a separable component of the vaporizer cartridge 120 or can be integrally formed with other component(s) of the vaporizer cartridge 120 (for example, formed as a unitary structure with the reservoir 140 and/or the like).

Figure 1F:
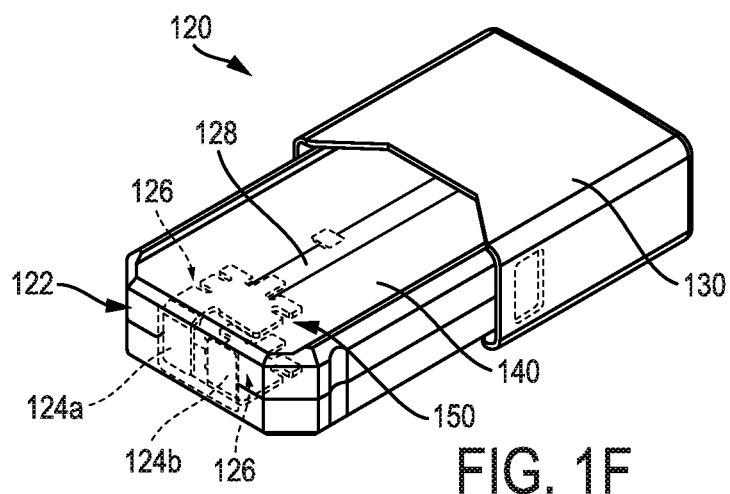
FIG. 1F is another perspective view of the vaporizer cartridge of FIG. 1E.

FIG. 1F shows additional features that can be included in the vaporizer cartridge 120 consistent with implementations of the current subject matter. For example, the vaporizer cartridge 120 can include a plurality of cartridge contacts (such as cartridge contacts 124a, 124b) disposed on the insertable end 122. The cartridge contacts 124a, 124b can optionally each be part of a single piece of metal that forms a conductive structure (such as conductive structure 126) connected to one of two ends of a resistive heating element. The conductive structure can optionally form opposing sides of a heating chamber and can act as heat shields and/or heat sinks to reduce transmission of heat to outer walls of the vaporizer cartridge 120. FIG. 1F also shows the cannula 128 within the vaporizer cartridge 120 that defines part of the airflow path 134 between the heating chamber formed between the conductive structure 126 and the mouthpiece 130.

As mentioned above, existing vaporizer devices can include an atomizer that includes separate wicking and heating elements to ultimately vaporize the vaporizable material to form a vaporized material. The wicking element draws the vaporizable material across its length. The wicking distance is therefore dependent upon, among other possible factors, the length of the wicking element itself. Further, the wicking distance can influence the ability of the vaporizer device to vaporize a desired amount of vaporizable material, such as when a user takes a puff on the vaporizer device.

In instances in which the atomizer includes a mesh, the mesh can function as either the wicking element or the heating element. Since electrical resistance of the mesh is typically low, when used as the heating element, a large amount of the mesh (along its length) is needed to provide sufficient electrical resistance for heating, such as ohmic heating. Under such circumstances, the mesh would not be suitable to also concurrently function as the wicking element because the length of the mesh would provide an overly long wicking distance for the vaporizable material to travel to be vaporized. Contrastingly, if the length of the mesh is tailored to a suitable wicking distance, the resulting mesh would not possess a sufficient amount of electrical resistance to also be used for heating, such as ohmic heating. Thus, since the electrical path and the capillary path of the meshes are not independent of each other, these meshes cannot be used as a combined wicking and heating element for the atomizer. Various features and devices are described below that improve upon or overcome these issues.

The vaporizer cartridges described herein use a combined wicking and heating element, thereby eliminating the need for two separate components to effect drawing and vaporizing of the vaporizable material. This combined wicking and heating element is a mesh that is sufficiently dimensioned to provide a length suitable for both wicking and heating. As discussed in more detail below, the mesh is in a folded configuration and positioned within an airflow tube that extends through a reservoir housing with a vaporizable material disposed therein. The mesh is configured to reduce wicking distance while still possessing a sufficient length for heating. That is, the meshes described herein possess a separate electrical path and capillary path which enables the mesh to function as both a wicking and heating element.

The cartridges generally include an airflow tube extending through the reservoir housing and a folded mesh that is disposed within the airflow tube. At least a portion of the airflow tube can be permeable to the vaporizable material, in which the permeable portion of the airflow tube can be configured to draw the vaporizable material from the reservoir housing into the airflow tube for vaporization. The permeable portion of the airflow tube can include a plurality of holes. The folded mesh can include a plurality of folds. The folded mesh can be configured to change from a deactivated state to an activated state in response to receiving an electric current. When in the activated state, the folded mesh can be configured to generate an amount of heat that is sufficient to vaporize at least a portion of the vaporizable material drawn from the reservoir housing. As used herein, "reservoir housing" is used synonymously with "reservoir."

Figure 2:
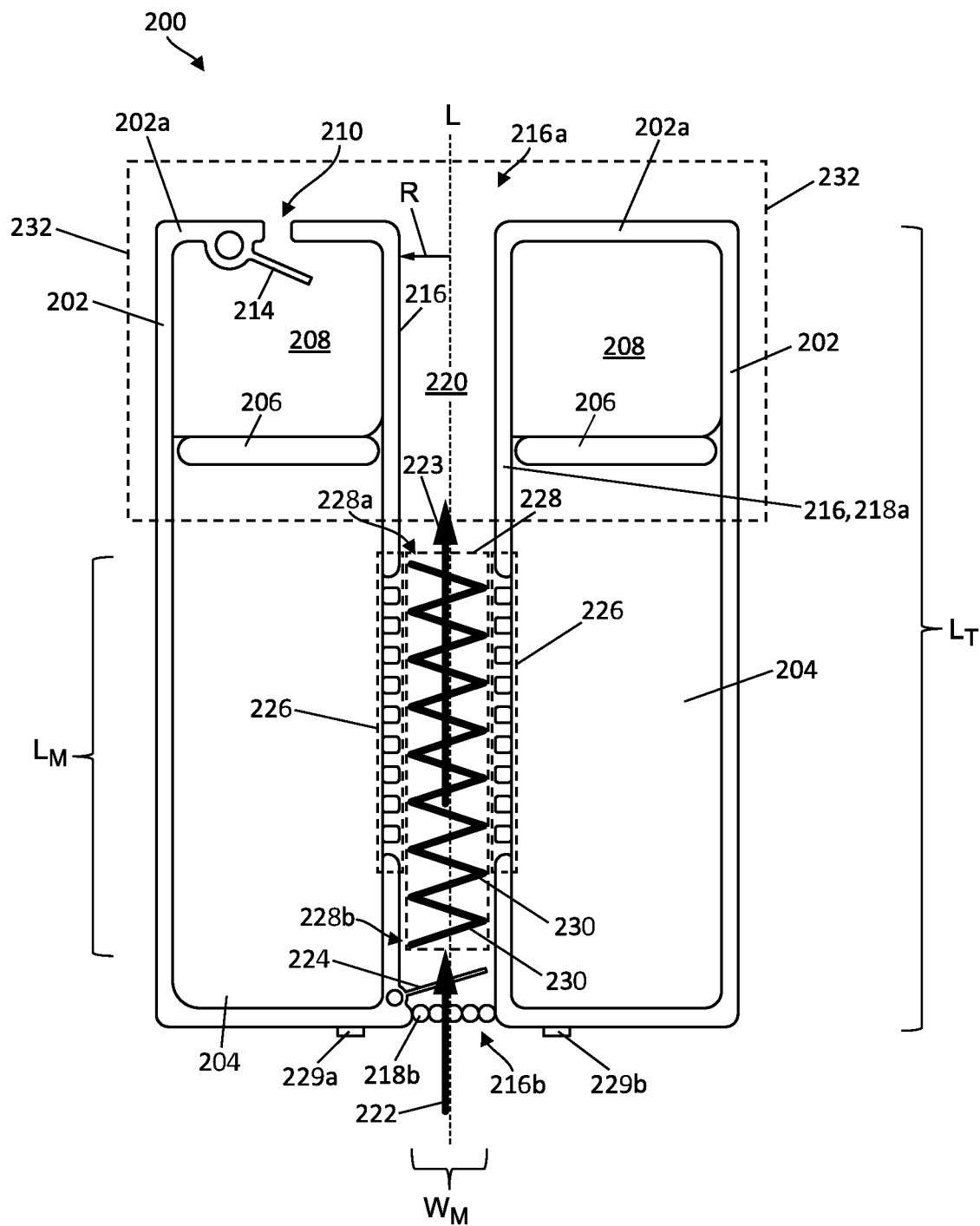
FIG. 2 illustrates a schematic cross-section view of another embodiment of a vaporizer cartridge.

FIG. 2 illustrates an exemplary vaporizer cartridge 200 that can be selectively coupled to and removable from a vaporizer body, such as vaporizer body 110 shown in FIGS. 1A-1D). More specifically, the cartridge 200 includes a reservoir housing 202, an airflow tube 216 extending through the reservoir housing 202, and a folded mesh 228 that is disposed within an airflow tube 216. For purposes of simplicity, certain components of the cartridge 200 are not illustrated.

While the reservoir housing 202 can have a variety of shapes and sizes, the reservoir housing 202, as shown in FIG. 2, is substantially rectangular in shape. The reservoir housing 202 is configured to hold a vaporizable material 204. As shown, a gasket 206 is disposed within the reservoir housing 202 and is configured to substantially control the vaporizable material 204 within the reservoir housing 202. Further, a headspace 208 exists between the gasket 206 and a top wall 202a of the reservoir housing 202. Thus, the gasket 206 separates the vaporizable material 204 from the headspace 208. The gasket can have a variety of configurations, such as a substantially rectangular shape that is dimensioned to fit within the reservoir housing 202 and allow the airflow tube to pass therethrough, as shown in FIG. 2. In other embodiments, a gasket 206 can be omitted.

In some embodiments, the reservoir housing 202 can include one or more vents, for example vent 210 as shown in FIG. 2, that are configured to substantially allow the passage of air into the reservoir housing 202 from the environment to thereby substantially maintain an inner pressure (e.g., an inner pressure that is substantially equal to ambient pressure) of the reservoir housing 202. As such, the one or more vents can function as a one-way valve and therefore can be used to decrease or eliminate negative pressure that is created as the vaporizable material 204 flows out of the reservoir housing 202.

Alternatively, or in addition, the reservoir housing 202 can include a valve 214 that is configured to allow airflow into the reservoir housing 202, as shown in FIG. 2. The valve 214 can also be configured to substantially prevent airflow from passing out of the reservoir housing 202. As such, the valve 214 can be configured as a one-way valve. This valve 214 can be a passive or active valve. This valve 214 can be mechanically and/or electronically controlled. Various configurations of the valve 214 are contemplated herein.

As shown in FIG. 2, the airflow tube 216 extends through the reservoir housing 202. While the airflow tube 216 is shown to be approximately centered within respect to a longitudinal axis extending through a centroid of the reservoir housing 202, such position is not required. As such, other locations of the airflow tube 216 within the reservoir housing 202 are also contemplated herein. Further, other airflow configurations through the reservoir housing 202 are also contemplated herein.

The airflow tube 216 can have a variety of configurations. For example, as shown in FIG. 2, the airflow tube 216 extends a length ($L_T$) from a first end 216a to a second end 216b and is defined by a curved sidewall 218a and a bottom wall 218b. The length of the airflow tube 216 is also referred to herein as tube length. Further, the airflow tube 216 defines a passageway 220 that extends therethrough. The airflow passageway 220 is configured to direct air, illustrated as arrow 222, through the airflow tube 216 so that the air 222 will mix with the vaporized material to form an aerosol, illustrated as arrow 223. The airflow passageway 220 further directs the aerosol 223 through the first end 216 (e.g., an outlet) of the airflow tube 216, and thus into a mouthpiece 232 that is coupled to the vaporizer cartridge 200, for inhalation by a user. While a mouthpiece 232 is shown in FIG. 2, a person skilled in the art will appreciate that in other embodiments, the mouthpiece 232 can be omitted and the user can directly puff on the cartridge 200 at an outlet (such as the first end 216 of the airflow tube 216).

As shown, the air 222 enters the airflow tube 216 through the bottom wall 218b as a user puffs the mouthpiece 232. As such, the bottom wall 218b is configured to allow airflow to readily pass therethrough and into the airflow tube 216. While the bottom wall 218b can have a variety of configurations, the bottom wall 218b is perforated, as shown in FIG. 2. The perforations can be of any suitable size that allows air to pass through the bottom wall 218b. In certain embodiments, the size of the perforations can substantially prevent any vaporizable material 204 and/or aerosol 223 present in the airflow tube 216 to pass through the bottom wall 218b. In this manner, undesirable leakage into other portions of a vaporizer body, such as vaporizer body 110 shown in FIGS. 1A-1D, coupled to the vaporizer cartridge 200, can be inhibited. The bottom wall 218b can include any suitable number of perforations, and therefore the number of perforations is not limited by what is illustrated in the FIG. 2. Alternatively or in addition, the bottom wall 218b can be formed of an air permeable material. Thus, the bottom wall 218b functions as an air inlet for the airflow tube 216.

The airflow tube 216 can also include a valve 224 that is configured to allow the airflow to enter the airflow tube 216 through the bottom wall 218b, as shown in FIG. 2. The valve 224 can also be configured to substantially prevent vaporizable material 204 within the airflow tube 216 from leaking through the bottom wall 218b. Alternatively, or in addition, the valve 224 can be configured to prevent air 222 and/or aerosol 223 within the airflow tube 216 from passing through the bottom wall 218b. As such, the valve 224 can be configured as a one-way valve. The valve 224 can be mechanically and/or electronically controlled. Various configurations of the valve 224 are contemplated herein.

Further, at least a portion of the curved sidewall 218a of the airflow tube 216 can be permeable to the vaporizable material 204. While the permeable portion of the curved sidewall 218a can have a variety of configurations, in this illustrated embodiment, as shown in FIG. 2, the permeable portion includes a plurality of holes 226 that extend through the curved sidewall 218a. These plurality of holes 226 can be configured to draw the vaporizable material 204 from the reservoir housing 202 into the airflow tube 216, and consequently into the passageway 220 thereof, for vaporization by the folded mesh 228, as discussed in more detail below. For example, as shown in FIG. 2, the plurality of holes 226 form a flow passageway that extends through the curved sidewall 218a of the airflow tube 216, and thus between the reservoir housing 202 and the passageway 220 defined by the airflow tube 216. The plurality of holes 226 can also have a variety of diameters that substantially allow vaporizable material 204 to flow from the reservoir housing 202 and into the airflow tube 216 until a pressure equilibrium is reached (e.g., when an internal pressure of the reservoir housing 202 is substantially equal to ambient pressure outside of the reservoir housing 202). Alternatively, the curved sidewall 218a of the airflow tube 216 can be formed of permeable material.

The plurality of holes 226 can be positioned along any portion of the curved sidewall 218a. For example, as shown in FIG. 2, the plurality of holes 226 are positioned proximate to the bottom wall 218b of the airflow tube 216. While the plurality of holes 226 are illustrated as being equidistant from one another, in other embodiments, the plurality of holes 226 can be spaced at different distances relative to each other and/or relative to the bottom wall 218b of the airflow tube 216.

As discussed above, a folded mesh 228 is disposed within the airflow tube 216. The folded mesh 228 can be configured to change from a deactivated state to an activated state in response to receiving an electric current. Further, when in the activated state, the folded mesh 228 can be configured to generate an amount of heat that is sufficient to vaporize at least a portion of the vaporizable material 204 drawn from the reservoir housing 202 through the plurality of holes 226 and into the airflow tube 216.

The folded mesh 228 can have a variety of configurations. For example, as shown, the folded mesh 228 includes a plurality of folds 230. The folded mesh 228, therefore, is formed from an unfolded mesh having a predetermined length and that possesses a sufficient amount of electrical resistance suitable for heating, such as ohmic heating. The folding decreases the length of the unfolded mesh but increases the width of the unfolded mesh to form the folded mesh 228. By increasing in width, a capillary path can be formed along the width of the folded mesh 228. As a result, the folded mesh 228 possesses an electrical path that extends along its length and a capillary path that extends along its width. The folded mesh 228 has a length ($L_M$) that extends from a first end 228a to an opposing second end 228b and a width ($W_M$) extending between adjacent folds. The folded mesh 228 can be formed of any suitable material capable of conducting an electric current. Non-limiting examples of suitable material include stainless steel and the like. In one embodiment, the folded mesh 228 is a concertina stainless steel mesh.

The folded mesh 228 can be positioned within any portion of the airflow tube 216. For example, as shown in FIG. 2, the folded mesh 228 is approximately centered with respect to a longitudinal axis (L) extending through a centroid of the cross-sectional area of the airflow tube 216. In other embodiments, the folded mesh 228 may be offset from the centroid. In some embodiments, the width ($W_M$) of the folded mesh 228 is greater than a radius (R) of the airflow tube 216, for example, as shown in FIG. 2.

Further, the folded mesh 228 extends along at least a portion of the length of the airflow tube 216. For example, as shown in FIG. 2, the folded mesh 228 extends along at least the portion of the airflow tube 216 having the plurality of holes 226. In some embodiments, the length of the folded mesh 228 can be less than the length of the airflow tube 216. In other embodiments, the length of the folded mesh 228 can be equal to the length of the airflow tube 216.

In some embodiments, the vaporizer cartridge 200 includes two or more cartridge contacts such as, for example, a first cartridge contact 229a and a second cartridge contact 229b. The two or more cartridge contacts can be configured to couple, for example, with the receptacle contacts 125a and 125b in order to form one or more electrical connections with the vaporizer body 110. The circuit completed by these electrical connections can allow delivery of electrical current to the folded mesh 228. The circuit can also serve additional functions such as, for example, measuring a resistance of the folded mesh 228 for use in determining and/or controlling a temperature of the folded mesh 228 based on a thermal coefficient of resistivity of the folded mesh 228.

In use, a pressure equilibrium can be created across at least a portion of the plurality of holes 226 between the reservoir housing 202 and the passageway 220 of the airflow tube 216 when the folded mesh 228 is in the deactivated state. As such, a portion of the vaporizable material 204 can be within the airflow tube 216 when the folded mesh 228 is in the deactivated state. The folded mesh 228 can be activated (changing from the deactivated state to the activated state) in response electric current being applied via a power source (not shown). Once activated, the folded mesh 228 generates heat that vaporizes at least a portion of the vaporizable material 204 in contact therewith, and in some instances, in close proximity thereto, into the vaporized material. This vaporized material then mixes with the air 222 that is passing through the passageway 220 of the airflow tube 216, and consequently between the plurality of folds 230 of the folded mesh 228, and forms aerosol 223. Alternatively, or in addition, the air 222 can pass through the folded mesh 228 itself.

A pressure differential can be created across at least a portion of the plurality of holes 226 between the reservoir housing 202 and the passageway 220 of the airflow tube 216 when the folded mesh 228 is in an activated state (e.g., in response to the vaporization of at least a portion of the vaporizable material 204 within the airflow tube 216 when the folded mesh 228 is in the activated state). It should be noted that this pressure differential can exist irrespective of whether the folded mesh 228 is in an activated state or a deactivated state. When a pressure differential is created, the vaporizable material 204 can flow from the reservoir housing 202 into the airflow tube 216 through the plurality of holes 226.

Terminology

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a," "an," and "the" are intended to include the plural forms as well, unless the context clearly indicates otherwise.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments, one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Use of the term "based on," herein and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described herein can be directed to various combinations and subcombinations of the disclosed features and/or combinations and subcombinations of several further features disclosed herein. In addition, the logic flows depicted in the accompanying figures and/or described herein do not necessarily require the particular order shown, or sequential order, to achieve desirable results. Other implementations may be within the scope of the following claims.

What is claimed is:

1. A cartridge for a vaporizer device, the cartridge comprising:
    a reservoir housing being configured to hold a vaporizable material;

an airflow tube extending through the reservoir housing, the airflow tube defining a passageway extending therethrough, at least a portion of the airflow tube being permeable to the vaporizable material, the permeable portion of the airflow tube being configured to draw the vaporizable material from the reservoir housing into the airflow tube for vaporization; and a folded mesh that is disposed within the airflow tube and includes a plurality of folds, the folded mesh having a capillary path and an electrical path such that the folded mesh is configured to draw vaporizable material directly from the reservoir housing and vaporize at least a portion of the drawn vaporizable material into vaporized material;

wherein the folded mesh is configured to change from a deactivated state to an activated state in response to receiving an electric current, and when in the activated state, the folded mesh is configured to generate an amount of heat that is sufficient to vaporize the at least a portion of the drawn vaporizable material into vaporized material; and wherein the capillary path extends along a width of the folded mesh, the width extending between adjacent folds of the plurality of folds, and wherein the electrical path extends a length of the folded mesh, the length extending from a first end to an opposing second end of the folded mesh.

2. The cartridge of claim 1, wherein the permeable portion of the airflow tube includes a plurality of holes.

3. The cartridge of claim 1, wherein the length of the folded mesh is less than a predetermined length of the folded mesh in an unfolded state.

4. The cartridge of claim 3, wherein the airflow tube has a tube length that extends from a first end to a second end, and wherein the tube length is greater than the length of the folded mesh.

5. The cartridge of claim 1, wherein the width of the folded mesh is greater than a radius of the airflow tube.

6. The cartridge of claim 1, wherein a pressure equilibrium is created across the permeable portion of the airflow tube between the reservoir housing and the passageway when the folded mesh is in the deactivated state.

7. The cartridge of claim 1, wherein a pressure differential is created across the permeable portion of the airflow tube between the reservoir housing and the passageway when the folded mesh is in the activated state.

8. The cartridge of claim 7, wherein the vaporizable material flows from the reservoir housing into the airflow tube through the permeable portion of the airflow tube when the pressure differential is created.

9. The cartridge of claim 7, wherein the pressure differential is created in response to the vaporization of at least a portion of the vaporizable material when the folded mesh is in the activated state.

10. The cartridge of claim 1, wherein a portion of the vaporizable material is within the airflow tube when the folded mesh is in the deactivated state.

11. A vaporizer device, comprising:
a vaporizer body; and
a cartridge that is selectively coupled to and removable from the vaporizer body, the cartridge including:

a reservoir housing being configured to hold a vaporizable material, an airflow tube extending through the reservoir housing, the airflow tube defining a passageway extending therethrough, at least a portion of the airflow tube being permeable to the vaporizable material, the permeable portion of the airflow tube being configured to draw the vaporizable material from the reservoir housing into the airflow tube for vaporization, and a folded mesh that is disposed within the airflow tube and includes a plurality of folds, the folded mesh having a capillary path and an electrical path such that the folded mesh is configured to draw vaporizable material directly from the reservoir housing and vaporize at least a portion of the drawn vaporizable material into vaporized material;

wherein the folded mesh is configured to change from a deactivated state to an activated state in response to receiving an electric current, and when in the activated state, the folded mesh is configured to generate an amount of heat that is sufficient to vaporize the at least a portion of the drawn vaporizable material into vaporized material; and wherein the capillary path extends along a width of the folded mesh, the width extending between adjacent folds of the plurality of folds, and wherein the electrical path extends a length of the folded mesh, the length extending from a first end to an opposing second end of the folded mesh.

12. The device of claim 11, wherein the vaporizer body includes a power source.

13. The device of claim 11, wherein the permeable portion of the airflow tube includes a plurality of holes.

14. The device of claim 11, wherein the length of the folded mesh is less than a predetermined length of the folded mesh in an unfolded state.

15. The device of claim 11, wherein the width of the folded mesh is greater than a radius of the airflow tube.

16. The device of claim 11, wherein a pressure equilibrium is created across the permeable portion of the airflow tube between the reservoir housing and the passageway when the folded mesh is in the deactivated state.

17. The device of claim 11, wherein a pressure differential is created across the permeable portion of the airflow tube between the reservoir housing and the passageway when the folded mesh is in the activated state.

18. The device of claim 17, wherein the vaporizable material flows from the reservoir housing into the airflow tube through permeable portion of the airflow tube when the pressure differential is created.

19. The device of claim 17, wherein the pressure differential is created in response to the vaporization of at least a portion of the vaporizable material when the folded mesh is in the activated state.

20. The device of claim 11, wherein a portion of the vaporizable material is within the airflow tube when the folded mesh is in the deactivated state.

* * * * *